United States Patent
Fitchmun (10) Patent No.: US 9,663,766 B2
(45) Date of Patent: May 30, 2017

(54) METHODS FOR PURIFYING ADENOVIRUS VECTORS

(71) Applicant: Bio-Rad Laboratories, Inc., Hercules, CA (US)

(72) Inventor: Mark Irwin Fitchmun, San Diego, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/808,699

(22) Filed: Jul. 24, 2015

(65) Prior Publication Data

US 2017/0022479 A1 Jan. 26, 2017

(51) Int. Cl.
*C12N 7/00* (2006.01)
*B01D 15/36* (2006.01)

(52) U.S. Cl.
CPC ............. *C12N 7/00* (2013.01); *B01D 15/362* (2013.01); *B01D 15/363* (2013.01); *C12N 2710/10051* (2013.01)

(58) Field of Classification Search
None
See application file for complete search history.

(56) References Cited

U.S. PATENT DOCUMENTS

| | | | | |
|---|---|---|---|---|
| 5,837,520 | A | * 11/1998 | Shabram | C07K 14/82 435/235.1 |
| 2004/0106184 | A1 | * 6/2004 | Senesac | C12N 7/00 435/239 |
| 2005/0158283 | A1 | 7/2005 | Zhang et al. | |
| 2009/0270596 | A1 | * 10/2009 | Gagnon | A61K 39/39591 530/387.1 |
| 2010/0055763 | A1 | 3/2010 | Zhang et al. | |
| 2010/0279385 | A1 | 11/2010 | O'Riordan et al. | |
| 2015/0024467 | A1 | 1/2015 | Sheldon et al. | |
| 2017/0022479 | A1 | * 1/2017 | Fitchmun | C12N 7/00 |

OTHER PUBLICATIONS

International Search Report and Written Opinion from Application No. PCT/US2016/043275, dated Oct. 24, 2016.

* cited by examiner

*Primary Examiner* — Shanon A Foley
(74) *Attorney, Agent, or Firm* — Kilpatrick Townsend & Stockton LLP (57) ABSTRACT

Methods of purifying an adenovirus from an impure preparation are provided. In some embodiments, a combination of mixed mode chromatography and anion exchange chromatography is used to purify the adenovirus.

20 Claims, 3 Drawing Sheets

METHODS FOR PURIFYING ADENOVIRUS VECTORS

BACKGROUND OF THE INVENTION

Large-scale downstream processing of viruses for clinical applications poses challenges which differ from those of many other biotherapeutics. These challenges arise in part from viral size and complexity. For example, the adenovirus vector contains over 2700 protein subunits with a mass of approximately 165 MDa and a diameter of about 0.1 µm. Further complexity is attributed to the tendency of adenovirus particles to be acid labile.

BRIEF SUMMARY OF THE INVENTION

Methods of purifying an adenovirus from an impure preparation are provided.

In some embodiments, the methods comprise:
(a) contacting an impure preparation comprising the adenovirus to a mixed mode chromatography support, wherein the mixed mode chromatography support is a hydrophobic cation exchange chromatography support, under conditions that allow the adenovirus to bind to the mixed mode chromatography support;
(b) eluting the adenovirus from the mixed mode chromatography support, thereby forming a mixed mode eluate;
(c) contacting the mixed mode eluate to an anion exchange chromatography support under conditions that allow the adenovirus to bind to the anion exchange support; and
(d) eluting the adenovirus from the anion exchange chromatography support.

In some embodiments, the adenovirus is a recombinant adenovirus. In some embodiments, the adenovirus is a serotype 5 adenovirus.

In some embodiments, the impure preparation comprises one or more contaminants selected from proteins, nucleic acids, incomplete virus particles, and adventitious viruses. In some embodiments, the impure preparation is a cell culture harvest and the contaminants comprise host cell proteins and host cell DNA.

In some embodiments, prior to step (a), the impure preparation comprising the adenovirus is treated with a nuclease. In some embodiments, in step (a), the impure preparation that is contacted to the mixed mode chromatography support is a cell culture harvest diluted in a buffer (e.g., at a ratio of about 1:1, about 1:2, about 1:3, about 1:4, or about 1:5). In some embodiments, the impure preparation has a pH of about 5.5 to about 7.0 when contacted to the mixed mode chromatography support.

In some embodiments, the methods further comprise, after step (a), washing the mixed mode chromatography support with a first wash solution, wherein the adenovirus remains bound to the mixed mode chromatography support. In some embodiments, the first wash solution comprises at least 1 mM histidine.

In some embodiments, in step (b) the eluting comprises raising the pH of the solution in contact with the adenovirus bound to the mixed mode chromatography support. In some embodiments, in step (b) the adenovirus is eluted from the mixed mode chromatography support with a buffer comprising at least 100 mM sodium chloride.

In some embodiments, in step (c) the mixed mode eluate has a pH of about 6.5 to about 8.5 when contacted to the anion exchange chromatography support. In some embodiments, in step (c), the mixed mode eluate that is contacted to the anion exchange chromatography support is diluted in a buffer (e.g., at a ratio of about 1:1, about 1:2, about 1:3, about 1:4, or about 1:5).

In some embodiments, the methods further comprise, after step (c), washing the anion exchange chromatography support with a second wash solution, wherein the adenovirus remains bound to the anion exchange chromatography support. In some embodiments, the second wash solution comprises at least 10 mM sodium chloride. In some embodiments, the methods further comprise, after washing with the second wash solution, washing the anion exchange chromatography support with a third wash solution, wherein the adenovirus remains bound to the anion exchange chromatography support. In some embodiments, the third wash solution comprises at least 100 mM sodium chloride.

In some embodiments, in step (d), the adenovirus is eluted from the anion exchange chromatography support with a buffer comprising at least 0.5 M sodium chloride.

In some embodiments, the purified product comprising adenovirus that is eluted in step (d) has at least 50% of the adenoviral activity of the initial impure preparation comprising adenovirus. In some embodiments, the purified product comprising adenovirus that is eluted in step (d) is substantially free of impurities. In some embodiments, the purified product comprising adenovirus that is eluted in step (d) is highly concentrated for adenovirus.

DEFINITIONS

As used herein, the term "adenovirus" or "Ad" refers to any adenovirus of the known seven subgenera of adenoviruses (classified as subgenera A through G). About 57 different serotypes of human adenoviruses exist. Serotype classification is typically based on hemagglutination and resistance to neutralization by antisera to other known adenovirus serotypes. In some embodiments, the adenovirus is adenovirus serotype 5 ("Ad5"). An adenovirus may be a wild-type virus, a modified virus (e.g., an attenuated virus), or a recombinant virus.

"Mixed mode chromatography support" refers to a solid phase chromatographic support that employs a combination of two or more chemical mechanisms in order to achieve separation of components such as proteins, DNA, and virus in a mixture. Examples include, but are not limited to, chromatographic supports that exploit combinations of cation exchange (i.e., in which the support is anionic), anion exchange (i.e., in which the support is cationic), hydrophobic interaction, hydrophilic interaction, hydrogen bonding, pi-pi bonding, and metal affinity. The solid phase can be a porous particle, nonporous particle, membrane, or monolith.

"Anion exchange chromatography support" refers to a solid phase chromatographic support that uses a positively charged ion exchange support that has an affinity for molecules having net negative surface charges in order to achieve separation of components. The solid phase can be a porous particle, nonporous particle, membrane, or monolith.

"Preparation" refers to any composition containing an adenovirus that is desired to be purified. In some embodiments, the preparation is an "impure" preparation. As used herein, the term "impure preparation" refers to a composition containing an adenovirus that is desired to be purified and one or more other components, such as but not limited to proteins, nucleic acids, lipids, various cell culture media components and additives, incomplete virus particles, and adventitious viruses.

DETAILED DESCRIPTION OF THE INVENTION

I. Introduction

It has been surprisingly discovered that an adenovirus can be purified using a two-step chromatography purification process to yield an active, concentrated virus product that has purity, host cell protein, and host cell DNA levels comparable to clinical grade products. The adenovirus purification processes described herein are readily scalable, use procedures and reagents that are compatible with current good manufacturing processes, and are sufficiently simple, rapid, and efficient to be used for the production of clinical grade viral vectors.

II. Chromatography Solid Supports

The methods of the present invention use a combination of forms of chromatography to achieve purification of adenovirus from an impure preparation. In some embodiments, a combination of mixed mode chromatography and anion exchange chromatography is used to purify the adenovirus. In some embodiments, a combination of hydrophobic cation exchange chromatography and anion exchange chromatography is used to purify the adenovirus.

The mixed-mode chromatography and anion exchange chromatography that are used in the methods of the present invention are operated in a bind-elute mode. "Bind-elute mode" refers to an operational approach to chromatography in which the buffer conditions are established so that target molecules to be purified (e.g., adenovirus), and optionally undesired contaminants or impurities, bind to the chromatography support when a preparation is applied to the chromatography support. Separation of the target molecule (e.g., adenovirus) can be achieved subsequently by changing the conditions such that the target molecule is eluted from the support. In some embodiments, contaminants or impurities remain bound following elution of the target molecule. In some embodiments, contaminants or impurities either flow through when the preparation is applied to the chromatography support, or are bound and eluted before elution of the target molecule.

The methods of the present invention utilize mixed mode chromatography for the purification of adenovirus. In some embodiments, the mixed mode chromatography support exploits a combination of cation exchange (i.e., negatively-charged moieties on the mixed mode support) and hydrophobic interaction, optionally with hydrogen bonding or pi-pi bonding interactions.

In some embodiments, the mixed mode ligand comprises at least one acidic moiety such as a carboxyl group, and also comprises at least one hydrophobic moiety such as, but not limited to, a phenyl ring or an aliphatic hydrocarbon chain. In some embodiments, the support is hydrophobic and weakly cationic. For example, in some embodiments, the mixed mode ligand comprises a carboxylic acid end group in combination with at least one hydrophobic moiety, such as an aromatic hydrophobic ring. Those skilled in the art will understand the definition of "strong" and "weak" ionic groups as those groups which are, or are not, respectively, capable of maintaining their charge across a wide pH range, such as pH 2 to pH 12. In some embodiments, the mixed mode ligand further comprises an amide bond serving as a hydrogen bond donor/acceptor.

In some embodiments, the mixed mode ligand is p-Aminohippuric acid. The p-Aminohippuric acid ligand is depicted in the following diagram:

A commercial example of the p-Aminohippuric acid ligand on a hydrophobic cation exchange support is Nuvia™ cPrime™, which is commercially available from Bio-Rad Laboratories, Inc. (Hercules, Calif.). Nuvia™ cPrime™ is described, for example, in Bio-Rad Laboratories, Inc. Bulletin 6418 (Rev A) and in Bio-Rad Laboratories, Inc. Bulletin 6242 (Rev C).

Other commercially available examples of hydrophobic cation exchange supports include, but are not limited to, Capto MMC™ (available from GE Healthcare). Mixed mode chromatography supports are also described, for example, in U.S. Pat. No. 7,999,085, the contents of which are incorporated by reference herein.

The methods of the present invention also utilize anion exchange chromatography for the purification of adenovirus. Anion exchange chromatography exploits positively charged functional groups on the support to bind to negatively charged molecules. Examples of suitable positively charged functional groups for use in anion exchange chromatography include, but are not limited to, secondary, tertiary, and quaternary amines (e.g., diethyl aminoethyl, dimethyl aminoethyl, trimethyl aminoethyl, and quaternary aminoethyl). The functional group can be attached to a solid support, such as by covalent binding.

The anion exchange chromatography support can be any weak or strong anion exchange chromatography support. In some embodiments, the anion exchange chromatography support comprises a strong ionic group. Structural groups that are useful as strong anionic exchange functionalities include, for example, quaternary amines (e.g., quaternary aminoethyl).

Commercial examples of anion exchange chromatography supports include, but are not limited to, Nuvia™ Q, UNOsphere™ Q, and UNO® Q (available from Bio-Rad Laboratories, Inc., Hercules, Calif.). Anion exchange chromatography support are also described, for example, in U.S. Pat. No. 8,138,291, the contents of which are incorporated by reference herein.

Any solid support can be used for mixed-mode chromatography and anion exchange chromatography. The solid support can be, for example, porous or non-porous and can be in the form, for example, of a matrix, bead, particle, chip, or other conformation, e.g., a membrane or a monolith, i.e., a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores.

The solid support can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, the mixed-mode chromatography support and the anion exchange chromatography support are each packed in a column.

In some embodiments, the mixed mode and/or anion exchange support is packed in a column of at least 5 mm internal diameter and a height of at least 25 mm. Such embodiments are useful, e.g., for evaluating the effects of various conditions on adenovirus purification. Other column dimensions may also be used.

In some embodiments, the mixed mode and/or anion exchange support is packed in a column of any dimension required to support preparative applications. Column diameter may range from less than 1 cm to more than 1 meter, and column height may range from less than 1 cm to more than 30 cm depending on the requirements of a particular application. Other column dimensions may also be used.

III. Adenoviruses and Preparations Containing Adenoviruses

The methods of the present invention can be used to purify any adenovirus, including wild-type adenovirus, a recombinant adenovirus, and modified adenovirus (for example, an adenovirus comprising a transgene). In some embodiments, the adenovirus is a recombinant adenovirus or a modified adenovirus. The adenovirus to be purified can be of any serotype. In some embodiments, the adenovirus is a serotype 5 adenovirus.

Methods of constructing and producing adenoviruses are known in the art. See, e.g., Palmer and Ng, "Methods for the Production of First Generation Adenoviral Vectors," in *Gene Therapy Protocols: Production and In Vivo Applications of Gene Transfer Vectors*, vol. 433, pages 55-78 (2008); see also, Ross et al., "Construction and Characterization of Adenovirus Vecotors," Cold Spring Harbor Protocols, 2009; doi:10.1101/pdb.prot5011. In some embodiments, cell cultures are inoculated with adenovirus particles and further cultured for a period of time (e.g., 24 to 48 hours) before harvesting the virus. Various methods of harvesting virus from cell culture are known in the art. In some embodiments, the adenovirus is harvested from the cell culture by lysing the cells (e.g., by mechanical or non-mechanical lysis methods). In some embodiments, the adenovirus is harvested from the cell culture by adding a cell permeation agent to release virus from host cells.

Any adenovirus preparation can be used in the present invention, including unpurified or partially purified adenovirus preparations from natural, synthetic, or recombinant sources. Unpurified adenovirus preparations can come from various sources including, but not limited to, bacterial lysates, yeast lysates, mammalian cell lysates, and cell harvests (e.g., by adding a cell permeation agent to release virus from host cells). Partially purified preparations can come from unpurified preparations that have been processed by at least one filtration, chromatography, precipitation, or fractionation step or any combination thereof. In some embodiments, the adenovirus preparation comprises a mammalian cell lysate. In some embodiments, the adenovirus preparation comprises a cell harvest of adenovirus released from mammalian host cells.

In some embodiments, the adenovirus preparation comprises one or more contaminants selected from proteins (e.g., host cell proteins), nucleic acids (e.g., host cell DNA), incomplete virus particles, and adventitious viruses (e.g., retroviruses). In some embodiments, the impure preparation comprises host cell proteins and host cell DNA.

In some embodiments, the impure adenovirus preparation comprising the adenovirus is subjected to a treatment step or purification step prior to contacting the impure preparation to the mixed mode chromatography support. As a non-limiting example, in some embodiments, the impure preparation (e.g., cell lysate or cell harvest) is subjected to a filtration or clarification step prior to contacting the preparation to the mixed mode chromatography support. Filtration methods and reagents are known in the art; see, e.g., WO 2011/045381 and US 2011/0207202. As another non-limiting example, in some embodiments, the impure preparation (e.g., cell lysate or cell harvest) is treated with a nuclease prior to contacting the preparation to the mixed mode chromatography support. Suitable nucleases for treating the impure preparation are commercially available and methods for treating the preparation with a nuclease are known in the art. For example, TurboNuclease™ (Accelagen) can be added to the impure preparation for at least one hour prior to the mixed mode chromatography purification step. In some embodiments, prior to contacting the impure preparation to the mixed mode chromatography support, the preparation can be subjected to a combination or two or more treatment or purification steps (e.g., a combination of a filtration or clarification step and a nuclease treatment step).

In some embodiments, the impure adenovirus preparation comprising the adenovirus is not subjected to a treatment or purification (e.g., filtration) step prior to contacting the impure preparation to the mixed mode chromatography support.

IV. Methods

The methods of the present invention utilize a combination of forms of chromatography to purify an adenovirus from an impure preparation, such as a preparation containing host cell proteins, host cell DNA, and/or incomplete viral particles. In some embodiments, the methods involve an initial mass capture of adenovirus from the impure preparation using a mixed mode chromatography support under suitable conditions as known in the art to allow the adenovirus to bind to the mixed mode chromatography support. The adenovirus is then eluted from the mixed mode chromatography support and subjected to a further purification process on an anion exchange chromatography support.

Mixed Mode Chromatography Step

In some embodiments, prior to contacting the impure preparation comprising adenovirus with the mixed mode chromatography support (e.g., a mixed mode column, e.g., a hydrophobic cation exchange chromatography column), the chemical environment inside the column is equilibrated. In some embodiments, the mixed mode support is equilibrated to establish an appropriate pH, conductivity, and/or concentration of salts. Equilibration of the support is accomplished, for example, by flowing an equilibration buffer containing appropriate reagents through the column. Buffering compounds may include, but are not limited to, histidine, phosphate, Tris, MES, HEPES, BICINE, and imidazole. In some embodiments, the equilibration buffer comprises histidine. In some embodiments, the equilibration buffer comprises histidine in an amount from about 1 mM to about 50 mM (for example, but not limited to, about 25 mM).

In some embodiments, the mixed mode chromatography support is equilibrated to a pH of about 4 to about 7. In some embodiments, the mixed mode chromatography support is equilibrated to a pH of about 5.5 to about 7 (e.g., about 5.5 about 6, about 6.5, or about 7). In some embodiments, the mixed mode chromatography support is equilibrated to a pH of about 6.

The impure preparation comprising the adenovirus can also be equilibrated to conditions compatible with the chromatography support equilibration buffer before applying the impure preparation to the chromatography support. In some embodiments, the impure preparation is equilibrated by adjusting the pH, the concentration of salts, or other compound as desired. In some embodiments, the impure preparation is equilibrated to a pH of about 4 to about 7. In some embodiments, the impure preparation is equilibrated to a pH of about 5.5 to about 7 (e.g., about 5.5 about 6, about 6.5, or about 7). In some embodiments, the impure preparation is equilibrated to a pH of about 6.

In some embodiments, the impure preparation is diluted in a buffer prior to applying the impure preparation to the chromatography support. In some embodiments, the impure preparation is diluted in a buffer that is the same as or that is compatible with the chromatography support equilibration buffer. In some embodiments, the impure preparation is diluted in an equilibration buffer that comprises histidine. In some embodiments, the impure preparation is diluted in buffer (e.g., equilibration buffer) at a ratio of about 1:1, about 1:2, about 1:3, about 1:4, or about 1:5 of impure preparation to buffer.

After the chromatography support and impure preparation have been equilibrated, the impure preparation can be contacted to the mixed mode chromatography support (e.g., column) under conditions that allow for the adenovirus to bind to the mixed mode support. In some embodiments, the impure preparation can be contacted to the column at a linear flow velocity in the range of, but not limited to, about 50-600 cm/hr, and in some embodiments, about 150-300 cm/hr. Other flow velocities can also be used.

Following binding of the adenovirus to the mixed mode chromatography support, the bound adenovirus is optionally washed with one or more agents under conditions in which the adenovirus remains substantially bound to the support, wherein the presence and amount of the agent or agents displaces and/or removes one or more contaminants (e.g., host cell protein, host cell DNA, incomplete virus particles, or adventitious viruses). A variety of washing agents can be used. In some embodiments, the agent is histidine or another salt. Other washing agents can also be used. In some embodiments, two, three, four, or more washing steps are carried out.

In some embodiments, the wash agent (e.g., histidine) is present at a concentration from about 1-100 mM. In some embodiments, the wash agent (e.g., histidine) has a concentration of about 25 mM. In some embodiments, the washing buffer has a pH that is the same or about the same as the pH of the equilibration buffer. For example, in some embodiments, the washing buffer has a pH of about 5.5 to about 7 (e.g., about 5.5 about 6, about 6.5, or about 7). In some embodiments, the washing buffer has a pH of about 6.

Following the optional washing step, the adenovirus is eluted from the mixed mode chromatography support. In some embodiments, the adenovirus is eluted by a combination of raising the pH of the solution in contact with the adenovirus bound to the support, and raising the ionic strength of the solution in contact with the adenovirus bound to the support (e.g., using a salt gradient). In some embodiments, the elution buffer has a pH of about 6.5 to about 9.5 (e.g., about 6.5, about 7, about 7.5, about 8, about 8.5, about 9, or about 9.5). In some embodiments, the elution buffer has a pH of about 6.5 to 8.5. In some embodiments, the elution buffer has a pH of about 8.5. In some embodiments, the elution buffer comprises sodium chloride or another neutral salt (e.g., potassium chloride, ammonium chloride, or sodium sulfate). In some embodiments, the elution buffer comprises sodium chloride or another neutral salt at a concentration of about 100-1000 mM (e.g., about 100, about 200, about 300, about 400, about 500, about 600, about 700, about 800, about 900, or about 1000 mM).

Some exemplary bind-wash-elute conditions for the mixed mode chromatography support step are:
binding condition: 0-50 mM histidine, pH 5.5-7 in a buffer
washing condition: 1-100 mM histidine, pH 5.5-7 in a buffer
elution condition: 100-1000 mM sodium chloride, pH 7.5-9.5, in a buffer (e.g., Tris or phosphate)

Elution from the mixed mode chromatography support yields a mixed mode eluate comprising a partially purified adenovirus.

Anion Exchange Chromatography Step

In some embodiments, the mixed mode eluate comprising a partially purified adenovirus is further purified using a second chromatography step of anion exchange chromatography. In some embodiments, prior to contacting the impure preparation comprising adenovirus with the anion exchange chromatography support (e.g., an anion exchange column), the chemical environment inside the column is equilibrated. In some embodiments, the anion exchange support is equilibrated to establish an appropriate pH, conductivity, and/or concentration of salts. Equilibration of the support is accomplished, for example, by flowing an equilibration buffer containing appropriate reagents through the column. Buffering compounds may include, but are not limited to, histidine, phosphate, Tris, MES, HEPES, BICINE, and imidazole. In some embodiments, the equilibration buffer comprises Tris or a combination of Tris and sodium chloride or another neutral salt. In some embodiments, the equilibration buffer comprises Tris in an amount from about 1 mM to about 100 mM (e.g., about 10, about 20, about 30, about 40, about 50, about 60, about 70, about 80, about 90, or about 100 mM). In some embodiments, the equilibration buffer comprises Tris in an amount from about 1 mM to about 100 mM (e.g., about 10, about 20, about 30, about 40, about 50, about 60, about 70, about 80, about 90, or about 100 mM) and comprises sodium chloride or another neutral salt in an amount from about 1 mM to about 300 mM (e.g., about 25, about 50, about 75, about 100, about 125, about 150, about 175, about 200, about 225, about 250, about 275, or about 300 mM).

In some embodiments, the anion exchange chromatography support is equilibrated to a pH of about 6.5 to about 9.5. In some embodiments, the anion exchange chromatography support is equilibrated to a pH of about 7.5 to about 9.5 (e.g., about 7.5, about 8, about 8.5, about 9, or about 9.5). In some embodiments, the mixed mode chromatography support is equilibrated to a pH of about 8.

The mixed mode eluate comprising the partially purified adenovirus can also be equilibrated to conditions compatible with the anion exchange chromatography support equilibration buffer before applying the mixed mode eluate to the anion exchange chromatography support. In some embodiments, the mixed mode eluate is equilibrated by adjusting the pH, the concentration of salts, or other compound as desired. In some embodiments, the mixed mode eluate is equilibrated to a pH of about 6.5 to about 9.5. In some embodiments, the mixed mode eluate is equilibrated to a pH of about 7.5 to about 9.5 (e.g., about 7.5, about 8, about 8.5, about 9, or about 9.5). In some embodiments, the mixed mode eluate is equilibrated to a pH of about 8.

In some embodiments, the mixed mode eluate is diluted in a buffer prior to applying the mixed mode eluate to the chromatography support. In some embodiments, the mixed mode eluate is diluted in a buffer that is the same as or that is compatible with the anion exchange chromatography support equilibration buffer. In some embodiments, the mixed mode eluate is diluted in an equilibration buffer that comprises Tris. In some embodiments, the mixed mode eluate is diluted in an equilibration buffer that comprises Tris and sodium chloride or another neutral salt. In some embodiments, the mixed mode eluate is diluted in buffer (e.g., equilibration buffer) at a ratio of about 1:1, about 1:2, about 1:3, about 1:4, or about 1:5 of mixed mode eluate to buffer.

After the chromatography support and mixed mode eluate have been equilibrated, the mixed mode eluate can be contacted to the anion exchange chromatography support (e.g., column) under conditions that allow for the adenovirus to bind to the anion exchange column. In some embodiments, the mixed mode eluate can be contacted to the column at a linear flow velocity in the range of, but not limited to, about 50-600 cm/hr, and in some embodiments, about 150-300 cm/hr.

Following binding of the adenovirus to the anion exchange chromatography support, the bound adenovirus is optionally washed with one or more agents under conditions in which the adenovirus remains substantially bound to the support, wherein the presence and amount of the agent or agents displaces and/or removes one or more contaminants (e.g., host cell protein, host cell DNA, incomplete virus particles, or adventitious viruses). A variety of washing agents can be used. In some embodiments, the agent is sodium chloride or another neutral salt (e.g., potassium chloride, ammonium chloride, or sodium sulfate). In some embodiments, the wash solution further comprises Tris in an amount from about 1 mM to about 100 mM (e.g., about 10, about 20, about 30, about 40, about 50, about 60, about 70, about 80, about 90, or about 100 mM).

In some embodiments, two, three, four, or more washing steps are carried out. In some embodiments, where more than one washing step is carried out, the washing agents can be the same or different. In some embodiments, where more than one washing step is carried out, the washing agents can be the same but the concentration of the agent that is used can be different for each washing step (e.g., using a lower concentration of the agent in a first washing step and a higher concentration of the agent in a second washing step). In some embodiments, where more than one washing step is carried out, the washing agents can be the same but the pH of the wash solution can be different for each washing step (e.g., using a lower pH wash solution for a first washing step and a higher pH wash solution for a second washing step). In some embodiments, where more than one washing step is carried out, the washing agents can be different for each step and the pH of the wash solution can be the same or different for each washing step.

In some embodiments, a first washing step on the anion exchange column is carried out using sodium chloride or another neutral salt at a concentration of about 10-500 mM. In some embodiments, the wash agent (e.g., sodium chloride) has a concentration of about 250 mM. In some embodiments, the wash solution has a pH that is the same or about the same as the pH of the equilibration buffer. For example, in some embodiments, the wash solution has a pH of about 6.5 to about 9.5, about 7.5 to about 9.5, or about 8.

In some embodiments, a second washing step on the anion exchange column is carried out in which the wash agent is the same as for the first washing step on the anion exchange column, but in which the concentration of the wash agent and/or the pH of the wash solution is different from the wash solution for the first washing step on the anion exchange column. For example, in some embodiments, the wash solution for the second washing step on the anion exchange column comprises sodium chloride or another neutral salt at a concentration of about 100-600 mM. In some embodiments, the wash agent (e.g., sodium chloride) has a concentration of about 450 mM. In some embodiments, the wash solution has a pH of about 6.5 to about 9.5, about 7.5 to about 9.5, about 7.5 to about 8.5, or about 8.

Following the optional washing step or steps, the adenovirus is eluted from the anion exchange chromatography support. In some embodiments, the adenovirus is eluted with a salt gradient (e.g., from 0 up to 2 M salt or higher). Other elution conditions can also be applied as desired, including, e.g., elution by inclusion of secondary modifiers, such as urea. In some embodiments, the adenovirus is eluted using an elution buffer comprising sodium chloride or another neutral salt (e.g., potassium chloride, ammonium chloride, or sodium sulfate) at a concentration of about 0.5-2 M (e.g., about 0.5, 0.6, 0.7, 0.8, 0.9, 1, 1.1, 1.2, 1.3, 1.4, 1.5, 1.6, 1.7, 1.8, 1.9, or 2 M).

Some exemplary bind-wash-elute conditions for the anion exchange chromatography support step are:
  binding condition: 0-100 mM Tris, pH 7-9, in a buffer
    first washing condition: 10-500 mM sodium chloride, pH 7-9, in a buffer (e.g., Tris or phosphate)

second washing condition: 100-600 mM sodium chloride, pH 7-9, in a buffer (e.g., Tris or phosphate)

elution condition: 0.5-2 M sodium chloride, pH 7-9, in a buffer (e.g., Tris or phosphate)

In some embodiments, the adenovirus that is eluted from the anion exchange chromatography support is substantially free of impurities. As used herein, "substantially free" means that the impurities are 10% or less of the purified adenovirus, e.g., less than 10%, 5%, 4%, 3%, 2%, 1%, 0.1%, 0.001%, or 0.0001%, as measured by parts per million virus particles. Various methods of assessing the purity of adenovirus are known in the art. For example, in some embodiments, the purity of the adenovirus that is eluted can be analyzed by gel electrophoresis (e.g., SDS-PAGE) and bands corresponding to viral structural proteins may be visualized by staining (e.g., Coomassie staining or SYPRO Ruby staining). The purity of the adenovirus that is purified can also be assessed by measuring the amount of host cell protein and/or host cell DNA contaminants, if any, that are present in the final purified product. The amount of host cell protein can be measured, for example, by immunoassay (e.g., ELISA) and the amount of host cell DNA can be measured, for example, by PCR (e.g., quantitative PCR against a housekeeping gene or ribosomal RNA gene).

In some embodiments, the final purified product that is eluted from the anion exchange chromatography support is highly concentrated for adenovirus as compared to the starting impure preparation. In some embodiments, the final purified product comprises adenovirus at a concentration of at least $10 \times 10^{10}$ virus particles/mL (e.g., at least $10 \times 10^{10}$, at least $20 \times 10^{10}$, at least $30 \times 10^{10}$, at least $40 \times 10^{10}$, at least $50 \times 10^{10}$, at least $60 \times 10^{10}$, at least $70 \times 10^{10}$, or at least $80 \times 10^{10}$ virus particles/mL). Methods of determining adenovirus concentration are known in the art. See, e.g., U.S. Pat. No. 7,316,898.

In some embodiments, the final purified product comprising adenovirus has at least 50%, at least 60%, at least 70%, at least 80% or more of the adenoviral activity of the starting impure preparation (e.g., cell lysate or cell harvest). Methods of measuring adenovirus activity are known in the art. See, e.g., U.S. Pat. No. 7,579,181. In some embodiments, the activity of the final purified product comprising adenovirus (e.g., eluate recovered from the anion exchange chromatography step) can be determined by comparing the infectivity before and after chromatography (e.g., comparing the infectivity of the impure preparation to the infectivity of the purified product). In some embodiments, adenovirus activity is measured using a hemagglutination assay. Hemagglutination assays are known in the art. See, e.g., Virocyt.com, "An Overview of Virus Quantification Techniques," published April 2013.

V. Kits

In another aspect, the invention provides a kit for use in the methods described herein. A kit can optionally include written instructions (e.g., on a CD-ROM or DVD) as well as packaging material. In some embodiments, the kits comprise (1) a prepacked mixed-mode chromatography support comprising hydrophobic and cation exchange moieties, and (2) a prepacked anion exchange support. Other reagents described herein in the context of the methods (e.g., equilibration, wash, and/or elution solutions) can also optionally be included in the kits.

VI. Examples

The following examples are offered to illustrate, but not to limit the claimed invention.

Purification of Adenovirus Using Mixed Mode and Anion Exchange Chromatography

Introduction

Adenovirus vectors are effective tools for the transfer of genetic material into mammalian cells. They offer several advantages including: the capacity to accommodate up to 37 kb of foreign genetic material; very high infection efficiencies, the ability to infect a wide variety of cell types, both dividing and non-dividing; their genome rarely integrates into the host chromosome; and current production systems are able to generate high virus titers. These and other qualities have led to considerable popularity of adenovirus vectors in both basic research and investigational gene therapy applications. In fact, adenoviruses are the most used gene transfer vectors in experimental therapies, accounting for one quarter of all gene therapy trials, and as of 2014, they had been used in almost 500 clinical trials.

Large scale downstream processing of viruses for clinical applications poses challenges which differ from those generally encountered with other biotherapeutics, such as proteins. These unique challenges arise, in part, from the virus's large size and complexity. In the case of adenovirus, one intact virus particle (vp) contains over 2700 protein subunits, has a mass of approximately 165 MDa, and a diameter on the order of 0.1 μm. The complexity of the particle gives rise thousands of charge variants, making it difficult to establish well defined binding and elution conditions on charged separation media. Its size prevents the use of nanofiltration for the removal of advantageous agents such as retroviruses. Also, adenoviruses tend to be acid labile, meaning that a low pH incubation is also unavailable as a tool for retrovirus clearance. It is difficult to use conventional electrophoretic methods to assess purity and monitor progress during downstream process development because the virus comprises many different types of protein. ELISAs and related methods have limited utility in monitoring product concentration and recovery during downstream process development because feed steams are rich in free virus components. Also, care should be taken to assure that the vector's genetic payload does not interfere with host cell DNA analysis.

Materials and Chromatography Methods

The virus used in this study, Ad5-E1+GFP, was a human adenovirus, serotype 5, with the E1a gene deleted and replaced with DNA coding for *Aequorea victoria* green fluorescent protein (GFP). The recombinant adenovirus was expanded in HEK-293 cells grown in HyClone DMEM/High Glucose+2% FBS. The cell cultures were inoculated with 3 foci forming units (FFU) units per cell.

Virus harvest, 36 hours after inoculation, was accomplished by adding a cell permeation agent (Somatek Inc.) to the culture (10 mL per liter of medium) to release virus from the host cells. Cells were then removed via 0.2 μm filtration. TurboNuclease (Accelagen) was added to the filtered harvest (at 200 μL/L), not less than one hour prior to chromatographic purification of the virus.

Data for both the mass capture (mixed mode chromatography) and the anion exchange operations was generated using Foresight pre-packed 8×100 mm (5.0 mL) columns. Flow rates were held constant at 1.0 mL/min. (=12 CV/hr=120 cm/hr).

Mixed Mode Chromatography:

A Nuvia™ cPrime™ hydrophobic cation exchange column was equilibrated with (25 mM histidine, pH 6.0). 60 mL of TurboNuclease treated virus culture supernatant blended with (25 mM histidine, pH 6.0) at a ratio of one part harvest to three parts buffer, and pumped over the column.

After loading, the column was washed with 24 mL (25 mM histidine, pH 6.0) and partially purified was eluted with (75 mM Tris, 525 mM NaCl, pH 8.5).

Anion Exchange Chromatography:

A Nuvia™ Q anion exchange column was equilibrated with (75 mM Tris, 250 mM NaCl, pH 8.0). The mixed mode eluate was blended with (75 mM Tris, pH 8.0) at a ratio of one part harvest to one part buffer and pumped over the column. After loading, the column was washed with 9 mL of (75 mM Tris, 250 mM NaCl, pH 8.0), followed by 15 mL of (75 mM Tris, 440 mM NaCl, pH 8.0). Purified virus was eluted using (75 mM Tris, 1000 mM NaCl, pH 7.5).

Virus Quantitation

FFU Determination:

Tenfold serial dilutions of virus samples were applied in quadruplicate to HEK-293 cells grown in 48-well tissue culture plates ($7 \times 10^4$ cells per well). Cultures were maintained for ten days and monitored for the appearance of virus induced cytopathic effect (CPE). TCID50 was then calculated using the Spearman & Kärber algorithm, and multiplied by 0.69 to determine the fluorescent forming unit (FFU) value.

Transgene Expression:

Three fold serial dilutions of virus samples were applied in triplicate to HEK-293 cells grown in 96-well tissue culture plates (60-90% confluent). 18 hours after the application of virus, the cells were lysed, and relative GFP concentrations were determined via fluorescent spectroscopy.

Total Virus:

Purified virus preparations (or dilutions thereof) were assessed spectrographically. Samples were mixed with an equal volume of 0.2% SDS, and absorbance was determined at 260 nm and 280 nm. Total virus concentration was determined using the following equation.

$$OD_{260} \times \text{dilution factor} \times 1.1 \times 10^{12} \text{ particles}$$

Note: Total virus measurements were used only when the criteria, $AU_{260} = 0.7 \pm 0.2$ and $AU_{260}/AU_{280} = 1.3 \pm 0.1$, were both met.

Reporting:

Select samples were analyzed by different methods in order to harmonize the different techniques. Except were otherwise indicated, virus quantities are provided as total virus particles, and concentrations are provided as vp/mL. The multiplicity of infection (MOI) was determined to be 48 vp/FFU.

Purity Assessments

Gel Electrophoresis:

SDS-PAGE analysis was performed using Criterion Tris-HCl 4-20% gradient gels (Bio-Rad Laboratories, Inc.) stained with Bio-Safe Coomassie stain (Bio-Rad Laboratories, Inc).

Host Cell Protein (HCP):

HCP levels were determined via a HEK-293 HCP ELISA kit (Cygnus Technologies)

Host Cell DNA:

DNA was extracted from test samples and subjected to quantitative PCR analysis using primers and probes directed against a 63 base pair region of the human 18S ribosomal RNA gene. Readouts were compared to a quantitative HEK-293 DNA standard curve. Q-PCR reactions were run and analyzed on an ABI Prism 7000 Sequence Detection System.

Results

Figure 1:
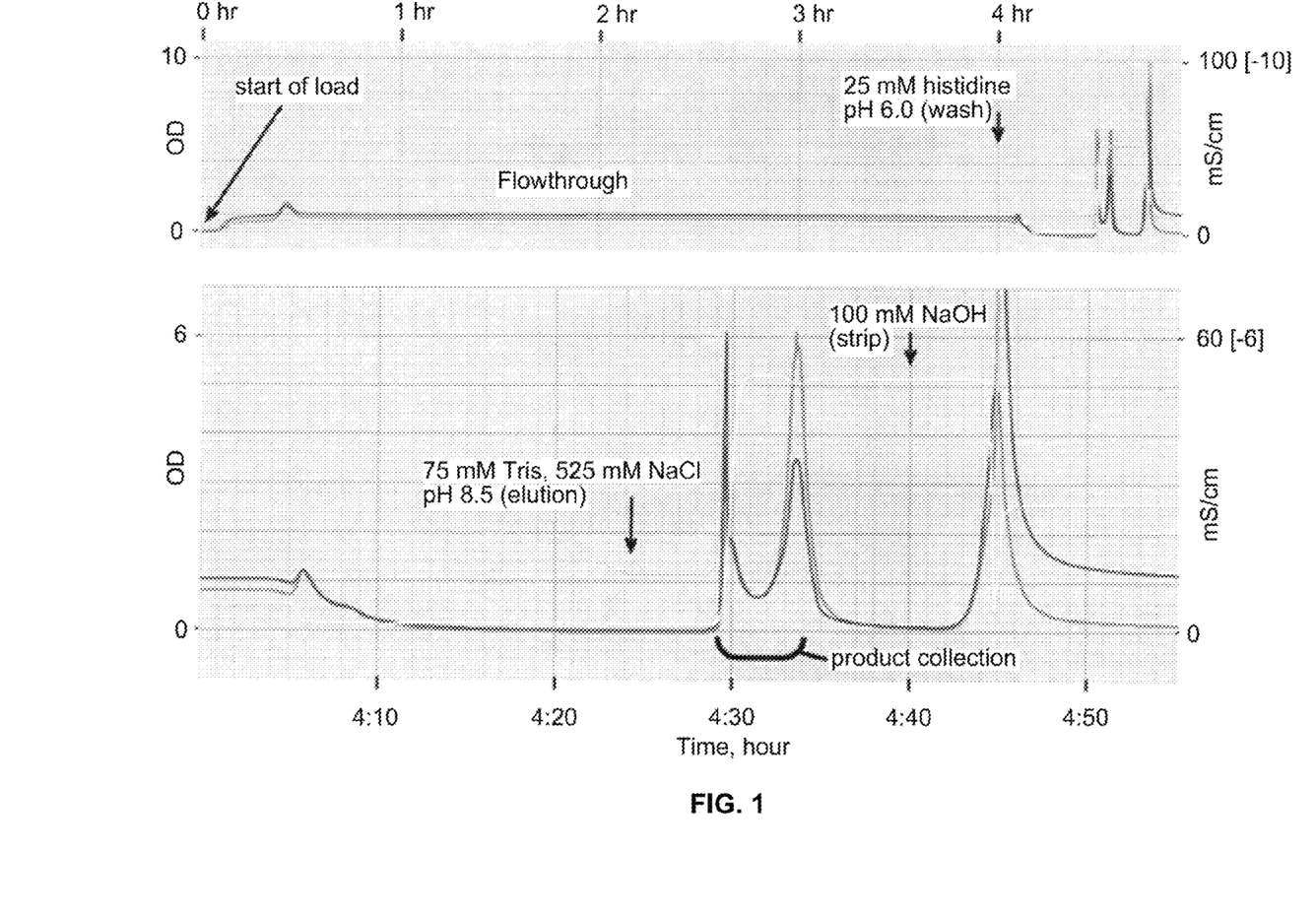
FIG. 1. Representative mixed mode chromatogram. A 5.0 mL Foresight Nuvia™ cPrime™ column was equilibrated with (25 mM histidine, pH 6.0). 60 mL of TurboNuclease treated virus culture supernatant blended with (25 mM histidine, pH 6.0) at a ratio of one part harvest to three parts buffer, and pumped over the column. After loading, the column was washed with 24 mL (25 mM histidine, pH 6.0) and partially purified adenovirus was eluted with (75 mM Tris, 525 mM NaCl, pH 8.5). The traces are OD at 260 nm (blue), OD at 280 nm (red) and conductivity (yellow).
Figure 3:
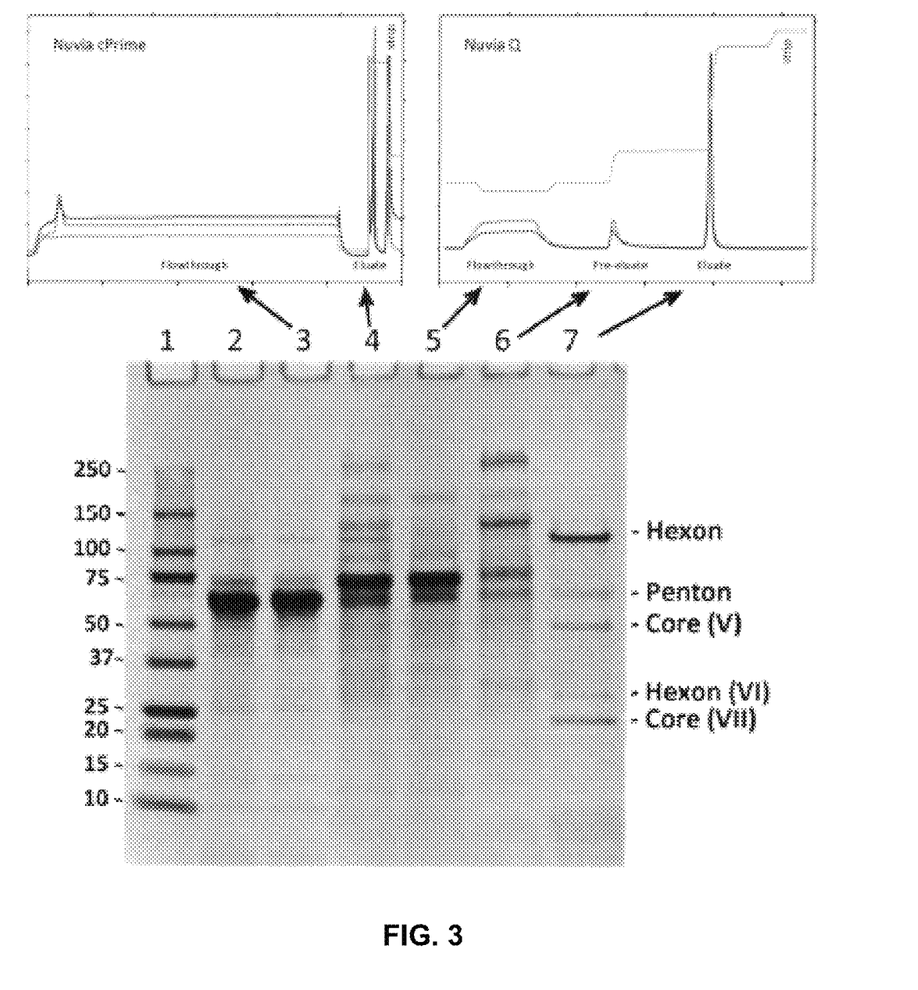
FIG. 3. SDS-PAGE of intermediates and final product. Lane 1=molecular weight markers. Lane 2=Nuvia™ cPrime™ load. Lane 3=Nuvia™ cPrime™ flowthrough. Lane 4=Nuvia™ cPrime™ elution/Nuvia™ Q load. Lane 5=Nuvia™ Q flowthrough. Lane 6=Nuvia™ Q pre-elution. Lane 7=Nuvia™ Q product. The five most prominent virus proteins (hexon, penton, core (V), hexon (VI), and core (VII)) are readily visible in the final product (lane 7).

Mass capture of the adenovirus was accomplished using Nuvia™ cPrime™ mixed mode resin (FIG. 1). This portion of the process achieved a 10 fold reduction in processing volume and a significant reduction in feedstream contaminants (FIG. 3, lanes 2 through 4).

A notable feature of chromatograms generated using the current procedure is a double peak following the application of the (75 mM Tris, 525 mM NaCl, pH 8.5) elution buffer (FIG. 1, lower panel). The first peak (4:29), is concurrent with the salt front, while the second (4:33) presumably corresponds to a pH shift. Both contained significant virus, and therefore product collection spanned both peaks. Neither increasing pH nor ionic strength alone achieved an elution with satisfactory recovery of virus.

Figure 2:
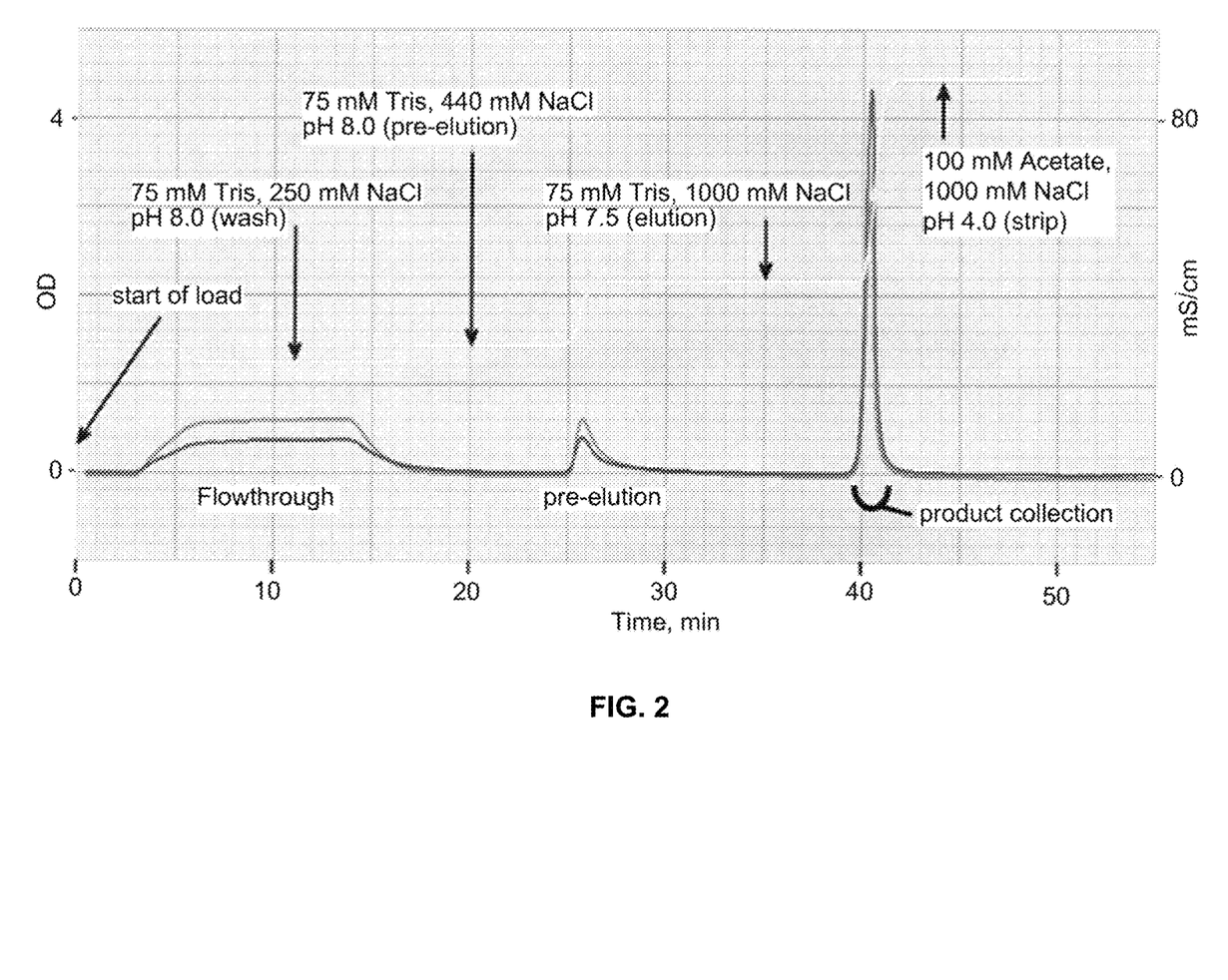
FIG. 2. Representative anion exchange chromatogram. A 5.0 mL Foresight™ A Nuvia™ Q anion exchange column was equilibrated with (75 mM Tris, 250 mM NaCl, pH 8.0). The mixed mode eluate was blended with (75 mM Tris, pH 8.0) at a ratio of one part Nuvia™ cPrime™ eluate to one part buffer and pumped over the column. After loading, the column was washed with 9 mL of (75 mM Tris, 250 mM NaCl, pH 8.0), followed by 15 mL of (75 mM Tris, 440 mM NaCl, pH 8.0). Purified virus was eluted using (75 mM Tris, 1000 mM NaCl, pH 7.5) The traces are OD at 260 nm (blue), OD at 280 nm (red) and conductivity (yellow).

Final virus purification was accomplished using Nuvia™ Q resin (FIG. 2). This portion of the process achieved an additional 2 fold reduction of product volume along with a significant improvement in product purity (FIG. 3, lanes 4 through 7). Following this operation, non-virus proteins were no longer evident by SDS-PAGE (FIG. 3, lane 7).

Each of the chromatographic operations was performed three times with comparable results.

Progress with respect to the removal of contaminating proteins can be visualized using SDS-PAGE (FIG. 3). Most evident in the virus culture harvest are cell culture media components such as albumin and transferrin (lane 2). The majority of protein from the harvest can be seen in the mixed mode flowthrough (lane 3), with the substantial enrichment of virus and less abundant contaminants in the mixed mode eluate (lane 4). During the anion exchange operation, virus is bound to the resin while contaminants either flowed through (lane 5), or are pre-eluted (lane 6). The five most prominent virus proteins; hexon, penton, core (V), hexon (VI), and core (VII); are readily visible in the final product (lane 7).

Virus concentration and DNA levels were evaluated at select points along the downstream process (Table 1). At harvest, virus was liberated from host cells by permeabilizing rather than lysing the cells. Cells were then removed by filtration. As a result, initial DNA as well as HCP levels were lower than is generally the case for adenovirus crude bulk harvests (rows 1 and 2). Endonuclease treatment of the clarified harvest further reduced detectable host DNA (row 2). After chromatographic purification of the virus (row 7), HCP levels were low, while host cell DNA was below the detectable limit.

TABLE 1

Virus and DNA concentrations of process intermediates and final product.

| sample | virus conc. × $10^{10}$/mL | volume mL | total virus × $10^{11}$ vp | HCP ng/ml | HCP ng/$10^{10}$ vp | DNA ng/ml | DNA ng/$10^{10}$ vp |
|---|---|---|---|---|---|---|---|
| 1 clarified bulk harvest | 5.1 | 60 | 30.6 | — | — | 3,080 | 3,144 |
| 2 nuclease treated harvest | 5.3 | 60 | 31.8 | 14,670 | 3,022 | 30 | 30 |

TABLE 1-continued

Virus and DNA concentrations of process intermediates and final product.

| sample | virus conc. × $10^{10}$/mL | volume mL | total virus × $10^{11}$ vp | HCP ng/ml | HCP ng/$10^{10}$ vp | DNA ng/ml | DNA ng/$10^{10}$ vp |
|---|---|---|---|---|---|---|---|
| 3 mixed mode flowthrough | 0.0 | 70 | — | 2,490 | | | |
| 4 mixed mode eluate | 30.6 | 6.0 | 18.4 | 880 | 58 | — | — |
| 5 anion ex. flowthrough | 0.0 | 15.0 | — | 170 | | — | |
| 6 anion ex. pre-elution | 0.0 | 2.0 | — | 360 | | — | |
| 7 anion exchange eluate | 81.8 | 2.0 | 16.4 | 160 | 2 | <1 | <0.02 |

CONCLUSION

The two-step chromatography process yields an active, concentrated virus product with purity, host cell protein (HCP), and DNA levels comparable to clinical grade products. The purification methods are expected to be applicable to recombinant adenoviruses in general, and to constructs derived from serotype 5 virus, in particular.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of purifying an adenovirus from an impure preparation, the method comprising:
   (a) contacting an impure preparation comprising the adenovirus to a mixed mode chromatography support, wherein the mixed mode chromatography support is a hydrophobic cation exchange chromatography support, under conditions that allow the adenovirus to bind to the mixed mode chromatography support;
   (b) eluting the adenovirus from the mixed mode chromatography support, thereby forming a mixed mode eluate;
   (c) contacting the mixed mode eluate to an anion exchange chromatography support under conditions that allow the adenovirus to bind to the anion exchange support; and
   (d) eluting the adenovirus from the anion exchange chromatography support.

2. The method of claim 1, wherein the adenovirus is a recombinant adenovirus.

3. The method of claim 1, wherein the adenovirus is a serotype 5 adenovirus.

4. The method of claim 1, wherein the impure preparation comprises one or more contaminants selected from proteins, nucleic acids, incomplete virus particles, and adventitious viruses.

5. The method of claim 4, wherein the impure preparation is a cell culture harvest and the contaminants comprise host cell proteins and host cell DNA.

6. The method of claim 1, wherein prior to step (a), the impure preparation comprising the adenovirus is treated with a nuclease.

7. The method of claim 1, wherein in step (a), the impure preparation that is contacted to the mixed mode chromatography support is a cell culture harvest diluted in a buffer.

8. The method of claim 1, wherein the impure preparation has a pH of about 5.5 to about 7.0 when contacted to the mixed mode chromatography support.

9. The method of claim 1, further comprising, after step (a), washing the mixed mode chromatography support with a first wash solution, wherein the adenovirus remains bound to the mixed mode chromatography support.

10. The method of claim 9, wherein the first wash solution comprises at least 1 mM histidine.

11. The method of claim 1, wherein in step (b) the eluting comprises raising the pH of the solution in contact with the adenovirus bound to the mixed mode chromatography support.

12. The method of claim 1, wherein in step (b) the adenovirus is eluted from the mixed mode chromatography support with a buffer comprising at least 100 mM sodium chloride.

13. The method of claim 1, wherein the mixed mode eluate has a pH of about 6.5 to about 8.5 when contacted to the anion exchange chromatography support.

14. The method of claim 1, wherein in step (c), the mixed mode eluate that is contacted to the anion exchange chromatography support is diluted in a buffer.

15. The method of claim 1, further comprising, after step (c), washing the anion exchange chromatography support with a second wash solution, wherein the adenovirus remains bound to the anion exchange chromatography support.

16. The method of claim 15, wherein the second wash solution comprises at least 10 mM sodium chloride.

17. The method of claim 15, further comprising, after washing with the second wash solution, washing the anion exchange chromatography support with a third wash solution, wherein the adenovirus remains bound to the anion exchange chromatography support.

18. The method of claim 17, wherein the third wash solution comprises at least 100 mM sodium chloride.

19. The method of claim 1, wherein in step (d) the adenovirus is eluted from the anion exchange chromatography support with a buffer comprising at least 0.5 M sodium chloride.

20. The method of claim 1, wherein the purified product comprising adenovirus that is eluted in step (d) has at least 50% of the adenoviral activity of the initial impure preparation comprising adenovirus.

* * * * *